(12) United States Patent
Baglini et al.

(10) Patent No.: US 8,220,928 B2
(45) Date of Patent: Jul. 17, 2012

(54) SYSTEM AND PROCESS FOR RECORDING ERG, PERG AND VEP MULTIFOCAL ELECTROFUNCTIONAL RESPONSES IN REAL-TIME

(75) Inventors: Claudio Baglini, Migliarno Pisano (IT); Gabriele Vestri, Florence (IT); Francesco Versaci, Prato (IT)

(73) Assignee: Contruzioni Strumenti Oftalmici S.r.l., Florence (IT)

( * ) Notice: Subject to any disclaimer, the term of this patent is extended or adjusted under 35 U.S.C. 154(b) by 110 days.

(21) Appl. No.: 12/386,443

(22) Filed: Apr. 18, 2009

(65) Prior Publication Data
US 2010/0091242 A1    Apr. 15, 2010

(30) Foreign Application Priority Data
Apr. 18, 2008  (IT) .................................. FI08A0081

(51) Int. Cl.
*A61B 3/00*  (2006.01)
*A61B 3/10*  (2006.01)
*A61B 3/14*  (2006.01)
*A61B 3/02*  (2006.01)

(52) U.S. Cl. ........ 351/246; 351/205; 351/206; 351/211; 351/237

(58) Field of Classification Search .................. 351/205, 351/222, 246, 206, 211, 237
See application file for complete search history.

(56) References Cited

U.S. PATENT DOCUMENTS

| | | | |
|---|---|---|---|
| 4,846,567 A | | 7/1989 | Sutter ........................... 351/224 |
| 6,022,107 A | | 2/2000 | Kutschbach et al. ......... 351/200 |
| 6,022,109 A | * | 2/2000 | Dal Santo ..................... 351/221 |

OTHER PUBLICATIONS

E. Brian Brown et al., "Contrast and luminance as parameters defining the output of the Veris topographical Erg", *Ophthalmic and Physiological Optics*, vol. 16, No. 1, Jan. 1996, pp. 42-48.
Erich E. Sutter et al., "The Field Topography of ERG Components in Man" *Vision Research*, Bd. 32, No. 3, 1992, pp. 433-446.
Michael F. Marmor, "Guidelines for basic multifocal electroretinography (mfERG)", *Documenta Ophthalmologica*, vol. 106, 2003, pp. 105-115.

* cited by examiner

*Primary Examiner* — Jack Dinh
(74) *Attorney, Agent, or Firm* — Pollack, P.C.

(57) ABSTRACT

Process and system for determining the topography of bioelectric response signals of a visual system including a patient's retina, optical nerve or a projection thereof at the level of the central cortex, following visual stimulation through a surface arranged in front of the patient's eye. An image which comprises a plurality of cells is displayed as stimuli, each cell being activated or deactivated according to a corresponding digital time function represented by a cyclical succession of binary m-sequences of duration (T) formed from a plurality of activation symbols (N). Symbols N have a duration (Ts), and the m-sequences of the various cells are obtained cyclically from a mother m-sequence. The process determines the total bioelectric response of the visual system. The response associated with each cell is determined by the total response of the visual system using a cross-correlation with a suitable translated version of a mother m-sequence. Calculation of the response of each cell is updated at the end of each symbol time (Ts), thereby making it possible to follow the evolution of the calculated response of each cell in real-time, without awaiting the end of an m-sequence.

17 Claims, 11 Drawing Sheets

| Seq. 1 | 0 | 1 | 0 | 0 | 1 | 1 | 1 |
| Seq. 2 | 1 | 0 | 1 | 0 | 0 | 1 | 1 |
| Seq. 3 | 1 | 1 | 0 | 1 | 0 | 0 | 1 |
| Seq. 4 | 1 | 1 | 1 | 0 | 1 | 0 | 0 |
| Seq. 5 | 0 | 1 | 1 | 1 | 0 | 1 | 0 |
| Seq. 6 | 0 | 0 | 1 | 1 | 1 | 0 | 1 |
| Seq. 7 | 1 | 0 | 0 | 1 | 1 | 1 | 0 |

SYSTEM AND PROCESS FOR RECORDING ERG, PERG AND VEP MULTIFOCAL ELECTROFUNCTIONAL RESPONSES IN REAL-TIME

FIELD OF THE INVENTION

This disclosure relates generally to ophthalmology and, more particularly, diagnosis of major ocular pathologies including, but not limited to, glaucoma, anomalies of vision and the retina, degeneration of the retinal structure, and retinal macular degeneration, as well as disorders of the optical nerve and visual cortex.

BACKGROUND OF THE INVENTION

Conventional ophthalmic diagnostic techniques are based on recording bioelectric responses generated by the retina, the optical nerve and all cellular and nerve processes including the central visual cortex, in association with a visual stimulus perceived by the patient. These bioelectric responses are recorded, through suitable electrodes arranged at the level of the conjunctival fornix, cornea, or, in the case of binocular recording, surface electrodes near the central visual cortex of both eyes, from which a biopotential can be obtained. The responses represen a measurement of the integrity of the visual system (density of cones, rods and cells connected thereto, gangliocytes, retinal cells, nerve fibres and visual cortex), or of possible alterations or destructive actions already caused by various pathologies.

Using current techniques (such as those set forth in: (i) U.S. Pat. No. 4,846,567 which issued on Jul. 11, 1989 to Sutter; (ii) E. B. Brown et al., Contrast luminance as parameter defining.... etc. Ophthalmic and physiological optic, Vol. 16, n. 1, January 1996, pp.42-48; and/or (iii) E. E. Sutter et al.: "The Field Topography of ERG Components in Man", Vision Research, Bd. 32, Nr. 3, 1992, Seiten 433-446) it is considered possible to record a number n of biopotentials (i.e., responses generated at different locations not just those from the retina) suitable for mapping the topography of the retina or central visual cortex.

Although widely used in current ophthalmologic diagnosis, this technique, it has been found, has limitations, including a lack of control of the retinal and/or consequently cortical areas actually stimulated, and the instant feedback of the resulting bioelectric responses recorded. In an attempt to stimulate and, thereby, record the biopotential generated by the ocular areas of interest, methodologies have been developed such as that set forth in E. E. Sutter et al., "The Field Topography of ERG Components in Man", Vision Research, Bd. 32, Nr. 3, 1992, Seiten 433-446. E. E. Sutter et al.s' method is based on stimulation through "m-sequences" and the subsequent decoding through cross-correlation between the stimulated area and the resulting biopotential (retinal or cortical reaction) recorded. While this technique has been found useful, it not only requires long and extended execution times, but also, in allowing possible artifacts (e.g., biopotentials induced by loss of focus or movements of the patient's eyes) to be monitored, does not allow for their rapid correction. This can the, in turn, adversely affect subsequent results, as is widely documented in the Guidelines for Basic Multifocal Electroretinography (mfERG) Documenta Ophthalmologica, n. 106, pp.105-115, 2003.

Other improvements in conventional techniques include fragmentation of the m-sequence into steps of shorter duration that allow an intermediate evaluation point for monitoring the accuracy of the result. A method of this general description is disclosed, for example, in U.S. Pat. No. 6,022,107, which issued on Feb. 8, 2000 to Ernst Kutschbach et. al. While this approach enables sampling, it has been found unreliable due to a discarding of automatism of the bioelectric responses exceeding predetermined size limits—to be repeated. This technique, in addition, requires a delay to the end of each m-sequence cycle for some repetitions to occur, thereby imposing long and unnecessary waiting times on the patient.

OBJECTS AND SUMMARY OF THE INVENTION

Accordingly, it is an object of this disclosure to provide a system and an apparatus that further improves quality control in the diagnosis of major ocular pathologies, thereby eliminating uncertainties in measurement due to intrinsic variability in the results during conventional clinical practice.

According to one aspect of the disclosure, a process is provided for determining the topography of bioelectric response signals of a visual system of a patient, the patient's retina, optical nerve or a projection thereof being at the level of the central cortex, following visual stimulation through a surface arranged in front of the patient's eye, wherein an image which comprises a plurality of cells is displayed as stimulation, each cell being activated or deactivated according to a corresponding digital time function represented by a cyclical succession of binary m-sequences of duration (T) formed by a plurality of activation symbols (N), each having a duration (Ts), the m-sequences of the various cells being obtained cyclically from a mother m-sequence, the process determining the total bioelectric response of the visual system, the response associated with each cell being determined by the total response of the visual system using a cross-correlation with a suitable translated version of a mother m-sequence, wherein calculation of the response of each cell is updated at the end of each symbol time (Ts), thereby making it possible to follow the evolution of the calculated response of each cell in real-time, without awaiting the end of an m-sequence.

In accordance with another aspect of the disclosure, a system is provided for determining the topography of bioelectric response signals of a visual system of a patient including the patient's retina, optical nerve or a projection thereof at the level of the central cortex, following visual stimulation, the system' comprising a display arranged in front of the patient's eye, a process connected to the display for showing an image, as stimulation, including a plurality of cells, each cell being activated or deactivated according to a corresponding digital time function represented by a cyclical succession of binary m-sequences of duration (T) formed by a plurality of activation symbols (N), each having a duration (Ts), the m-sequences of the various cells being obtained cyclically from a mother m-sequence, the system further comprising a sensor and amplifier for determining the total bioelectric response of the visual system, and recording the response on the processor, such that the response associated with each cell is determined by the total response of the visual system using a cross-correlation with a suitable translated version of a mother m-sequence, wherein the processor updates the calculation of the response of each cell at the end of every symbol time (Ts), thereby making it possible to follow the evolution of the calculated response of each cell in real-time, without having to wait for the end of an m-sequence.

BRIEF DESCRIPTION OF THE DRAWINGS

A specific, illustrative system and process for recording ERG, PERG, VEP and multifocal electrofunctional responses in real-time, according to this disclosure, is described below with reference to the accompanying drawings, in which.

The same numerals are used throughout the drawing figures to designate similar elements. Still other objects and advantages of the present invention will become apparent from the following description of the preferred embodiments.

DETAILED DESCRIPTION OF THE PREFERRED EMBODIMENTS

Figure 1A:
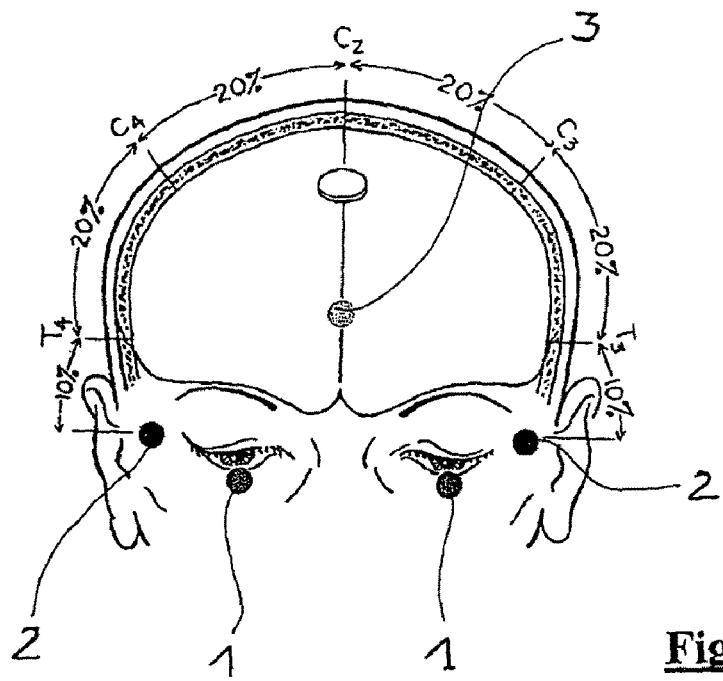
FIGS. 1a and 1b show an arrangement of electrodes, on the face and head of a patient, for recording retinal and cortical biopotential, according to one aspect of the disclosure.
Figure 1B:
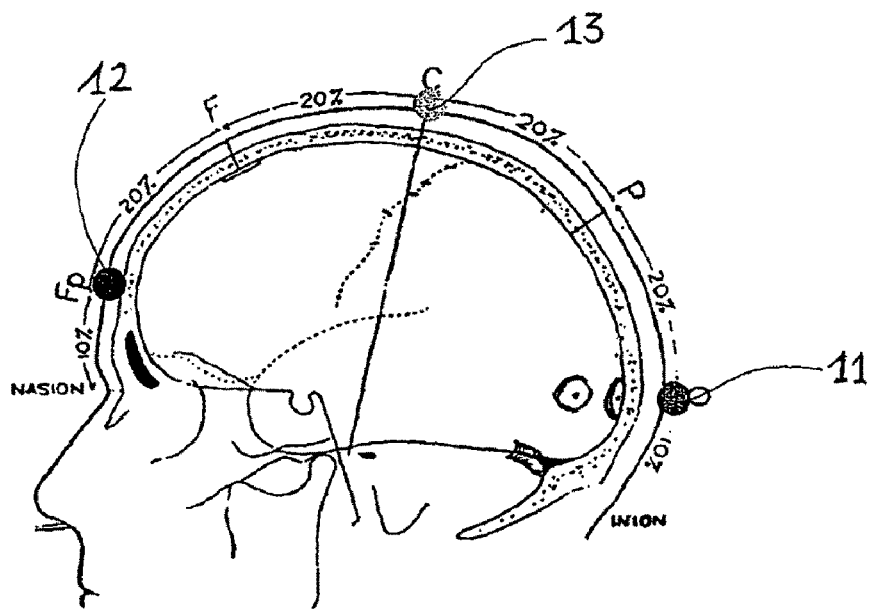

Referring now to the drawings and, more particularly, to FIGS. 1-10, there is shown generally a specific, illustrative system and process for recording ERG, PERG and VEP multifocal electrofunctional responses in real-time, according to various aspects of the present invention. In one example, illustrated generally in FIGS. 1a, 1b, 2 and from 4a-4h, a configuration of electrodes is arranged on the face of a patient to be examined, as in conventional ERG, PERG and VEP recording techniques. Specifically, in case of retinal biopotential (FIG. 1a), an active exploring electrode is inserted inside the lower conjunctival fornix (positions 1) or on the corneal surface of each eye, the electrode coming into contact with the eyeball or also at the level of the central visual cortex using surface electrodes, so as to detect a bioelectric signal generated by the stimulated areas. Preferably, to record the retinal biopotential, the electrode is of the HK LOOP type, which comprises a very thin silver wire coated with a sheath constructed, e.g., of TEFLON, on which some incisions are made to allow contact with the patient's eyeball.

This type of electrode has been found particularly advantageous in that, ulike conventional corneal electrodes, it does not interfere with the patient's vision, and because it allows the patient to blink comfortably during use. Moreover, because a superior contact impedance is provided between the electrode and the patient and thus a more reliable contact than that of cutaneous electrodes, refractive problems often associated with the use of corneal electrodes is avoided. In addition, by the present invention, it is now possible to record bioelectric signals with a very high signal to noise ratio. This reduces substantially the number of samples to be taken and, hence, the time taken for examination of the patient's eye(s).

Initially in operation, after the patient's skin has been suitably cleaned, a reference electrode is positioned at the level of the outer temporal corner of each eye (e.g., at position 2, FIG. 1a) of the patient. The electrode preferably comprises a silver or silver chloride disc to which a special electroconductive paste is applied to assist in contact with the patient's skin. A common electrode, desirably of the same type as the reference electrode, is then arranged at the center of the patient's forehead (e.g, position 3). In the case of cortical detection, an active exploratory electrode, a reference electrode, and a common electrode, for instance, are positioned according to the configuration indicated at positions 11, 12 and 13, respectively, of FIG. 1b.

Figure 2:
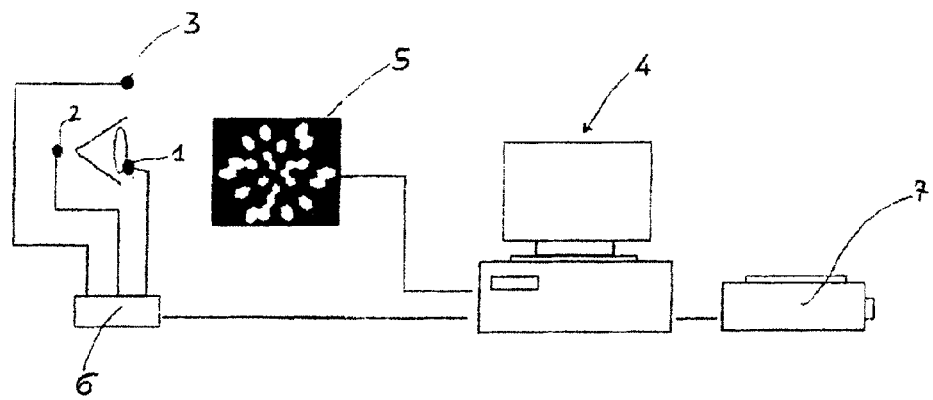
FIG. 2 illustrates schematically hardware of a system, according to one aspect of the disclosure.

Next, the patient is positioned a selected distance, e.g., about 30 cm, from an apparatus for performing the examination, with the patient's chin resting on an adjustable chin-rest. Such apparatus, as shown in FIG. 2, comprises a personal computer 4 having a software system suitable (i) for managing simultaneously a generation of a sequence of visual stimuli shown on a screen 5 arranged at a height of the patient's eyes, and (ii) for recording the resulting biopotential. In accordance with what is shown and described herein with respect to conventional apparatuses, the average brightness of the screen is preferably calibrated according to the type of examination and preselected values.

In accordance with one aspect of this disclosure, recording of the biopotential takes place, for example, through the use of a differential amplifier 6 operatively connected both to personal computer 4 and to electrodes 1, 2, 3 (or, alternatively, 11, 12, 13). Such a differential amplifier is characterized by a passband of between about 0.1 Hz and about 3000 Hz and an amplification factor generally within a range of 50,000 V/v and 500,000 V/v. A 16 bit A/D converter (not shown) is preferably provided for digitizing the signal, all according to conventional applications.

The software residing on the personal computer, above and beyond allowing the recorded biopotential to be processed, also controls the generation of pattern stimuli presented on screen 5. The biopotential to be processed is printable using a printer 7. The stimuli are configured on the screen as shown, for example, in FIGS. 4a to 4d. In operation, the patient is shown a sequence of cell patterns, i.e., a group of visual stimuli having various spatial and temporal forms. In synch with the stimulus, the system acquires the sampled signal to be processed (namely, a bioelectric response associated with presentation of a visual stimulus) from electrodes suitably positioned on the patient. Each cell on the screen is then modulated based upon a corresponding binary m-sequence, as described in detail below.

An objective of the examination is ultimately to associate a bioelectric response with every cell belonging to the stimulation pattern, i.e., to the retinal portion or cortical projection associated with such cell.

Figure 4A:
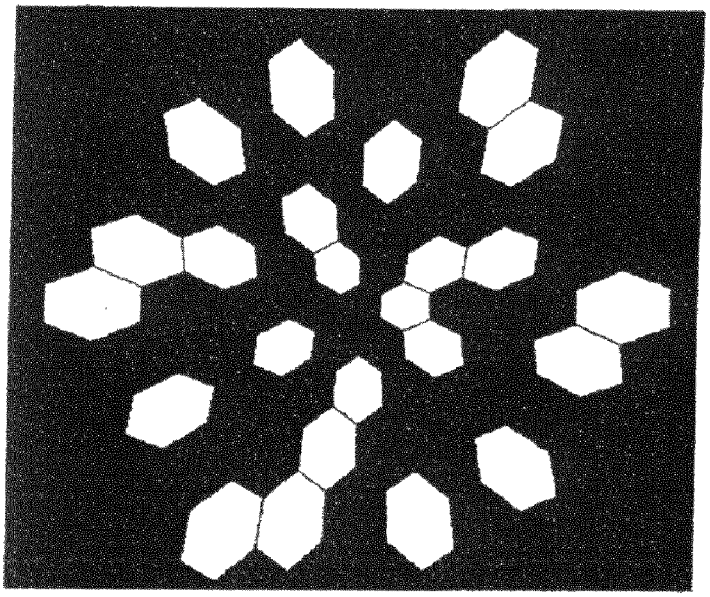
FIGS. 4a-4h show respective examples of pattern stimuli according to the process of the disclosure.

For MF-ERG examination, the term "activated" desirably means "lit" and "deactivated" is preferably interpreted as "not lit" (See FIG. 4a, in which some cells are lit, and others are not). For MF PERG and VEP examinations, on the other hand, the word "activated" can mean placed in the "normal pattern condition", and "deactivated" as may be construed to mean placed in the "inverse pattern condition" (FIG. 4c, in which some cells have a normal pattern, while others have an inverse pattern).

Figure 4B:
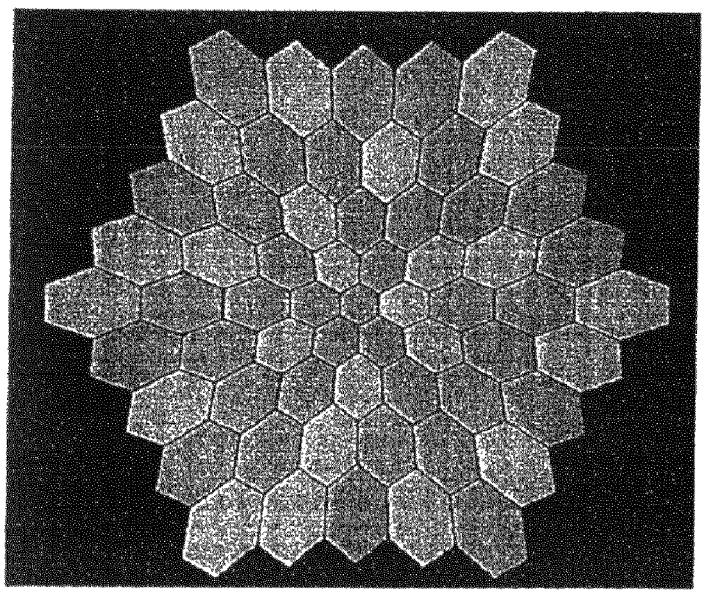
Figure 4C:
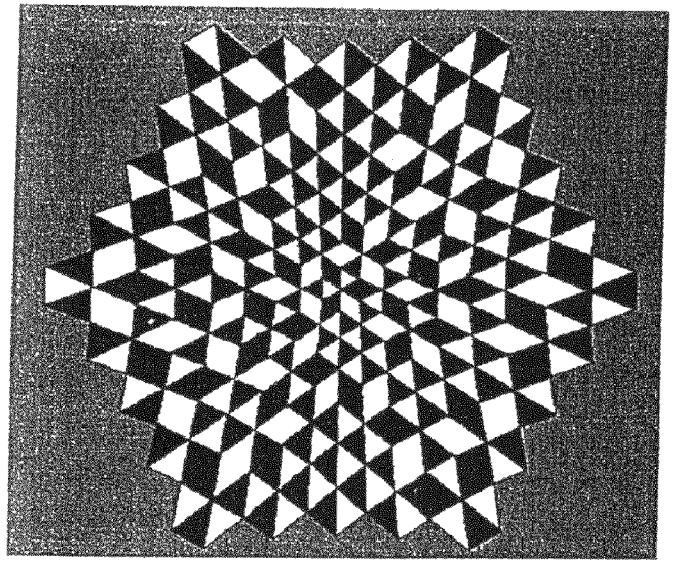
Figure 4D:
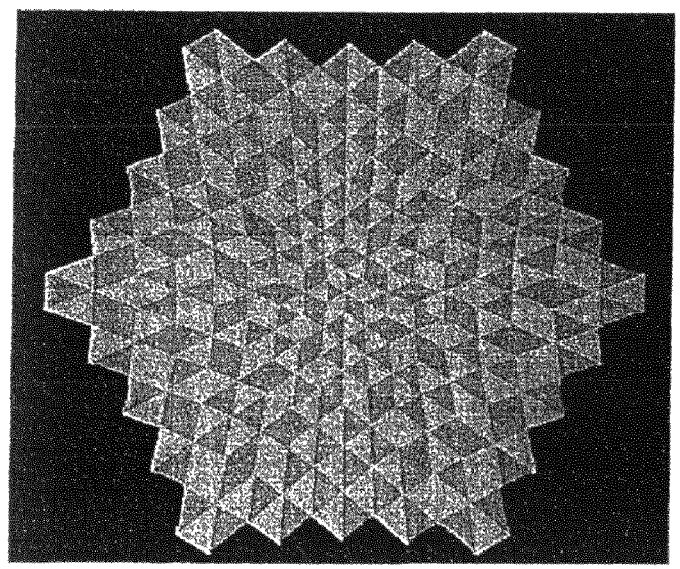

As illustrated in FIGS. 4b and 4d, it is also possible to modify the characteristics of the images, for example, color, brightness and contrast as well as shape, spatial size, temporal alternation, distortion and visual angle subtended. In this manner, the n number of retinal or relative cortical areas that result from the type of multifocal stimulus used can be stimulated independently.

Figure 4E:
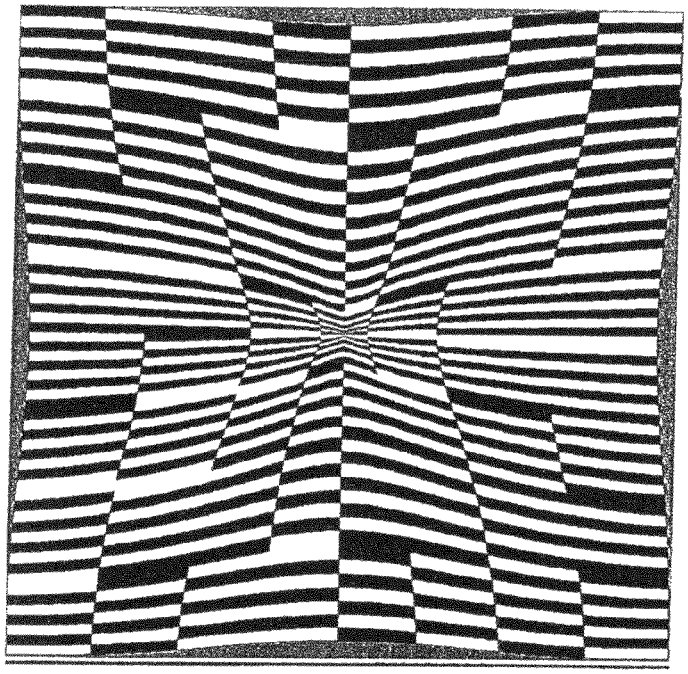
Figure 4F:
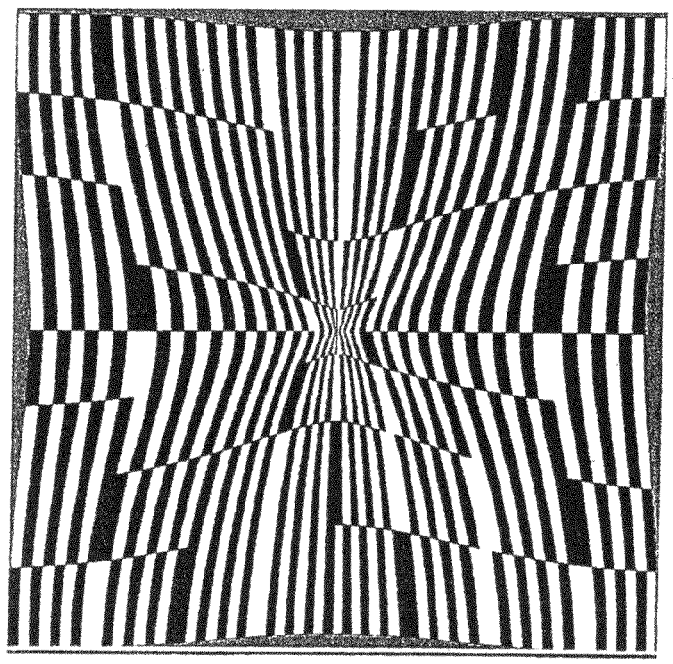
Figure 4G:
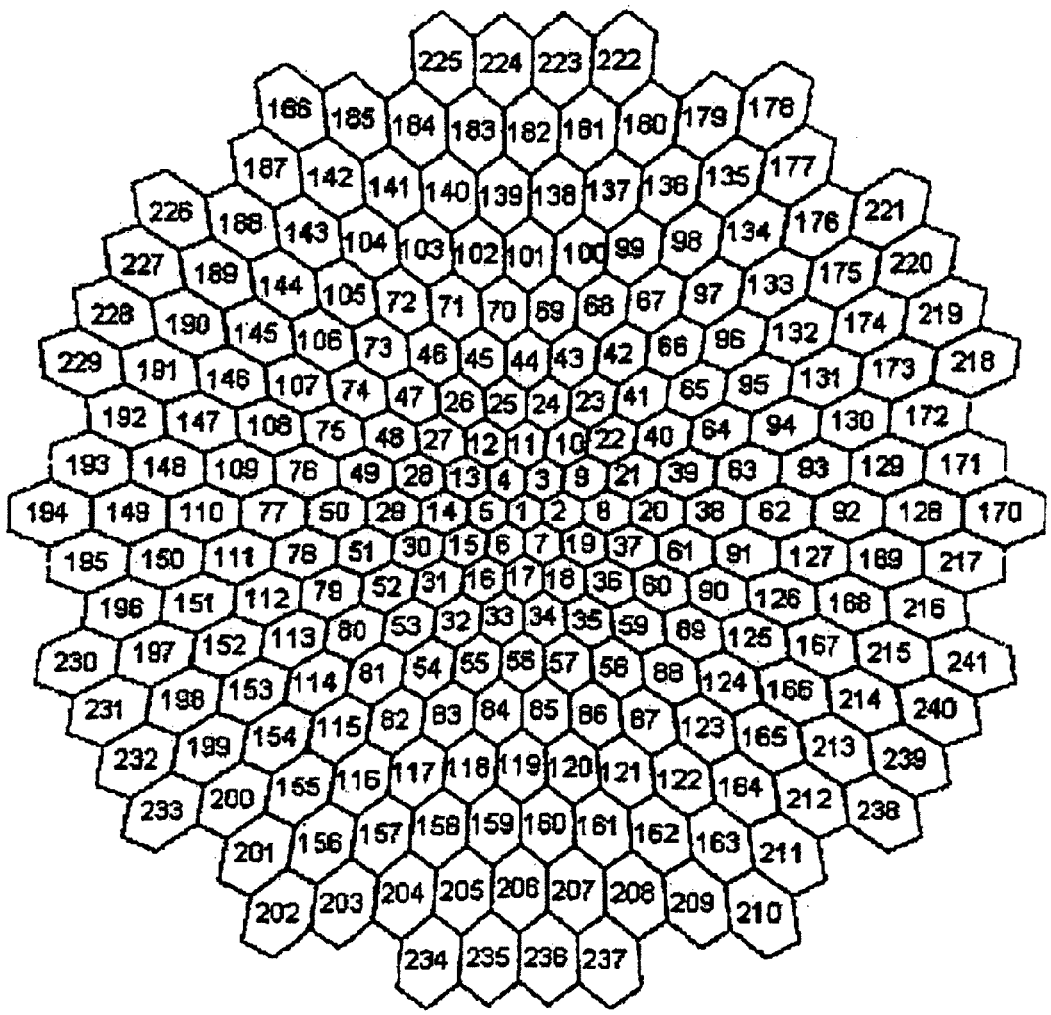
Figure 4H:
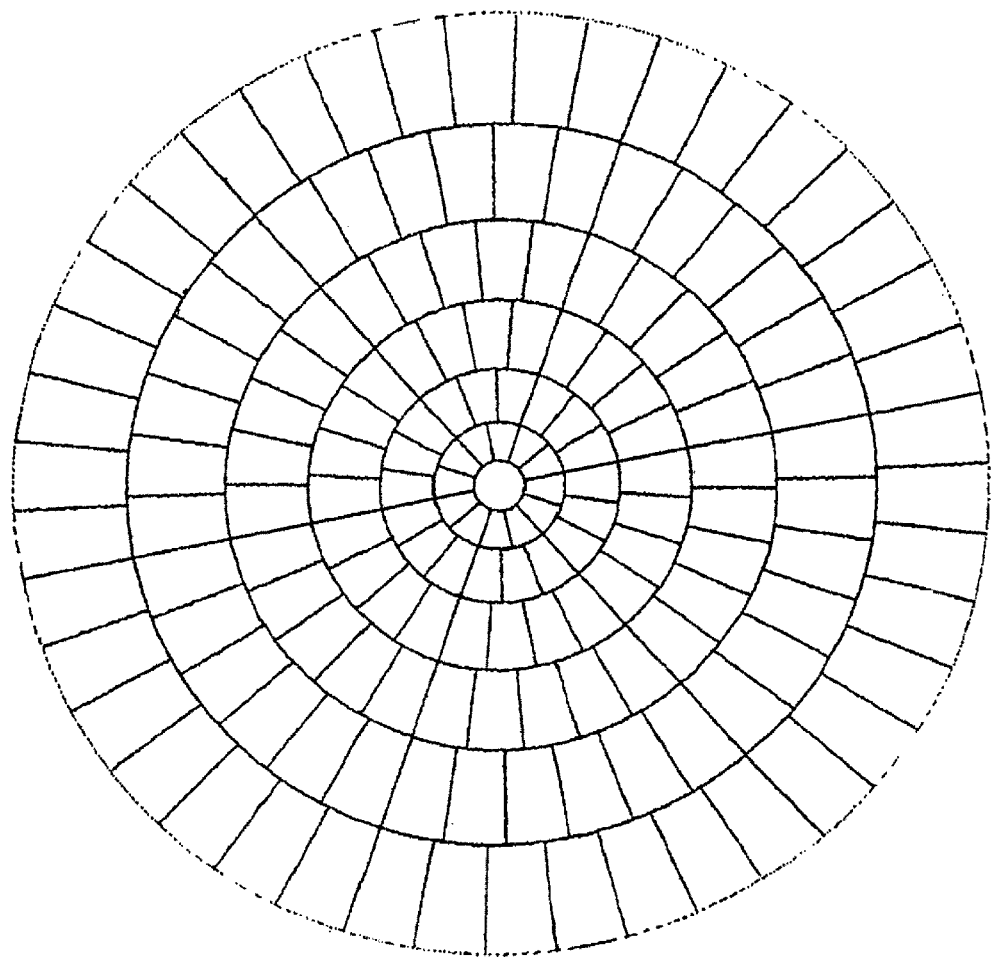

In addition, FIGS. 4e and 4f show a different set of stimuli suitable for selectively stimulating visual areas or retinal and cortical receptive fields, both horizontally and vertically. FIG. 4g represents a another stimulus set, this one made up of a plurality of cells (hexagons) suitable for stimulating a different number of visual areas or retinal and cortical receptive fields. Finally, FIG. 4h shows a distinct set of images made up of a plurality of cells divided into sectors of concentric rings. The rings are further divided into white-black elements or contrasting colors suitable for stimulating visual areas or retinal and cortical receptive fields.

Turning now, more particularly, to the control of stimulation, recording of the biopotential and, therefore, measurement of the retinal or cortical biopotential, specifically for the n areas stimulated, takes place as follows.

First, the m-sequence is a sequence of symbols 1 and −1 of length $N=2^s-1$, where s is a positive whole number. If the m-sequence is N symbols long, then it is possible to manage a pattern of M cells (M<N). Each cell is associated with an m-sequence N symbols long that can be obtained by cyclically translating a mother m-sequence. The various m-sequences generated through cyclic translation of a mother m-sequence are pseudo-orthogonal, as indicated in the example diagram shown is FIG. 6 (s=3, N=7).

Ts is the duration or symbol time period of the m-sequence, i.e., of 1 or −1. T is the length of time for an entire m-sequence, i.e., a symbol time multiplied by the length of the m-sequence N. Assuming that k periods of time Ts have elapsed since commencement of the m-sequence, if the q-th m-sequence associated with the q-th cell contains a 1 in the k-th position, then the cell of the pattern on the screen will be activated. If not, then the cell is deactivated. Notably, the length of time between two stimuli is selected so as to be long enough to span the entire bioelectric response for such time.

Figure 8:
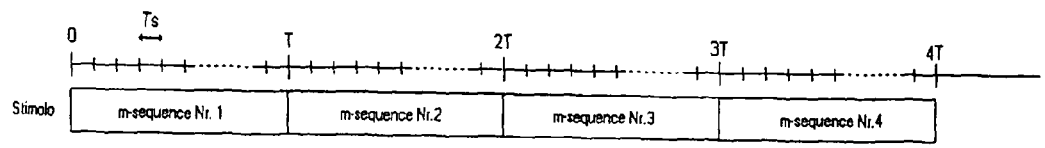
FIG. 8 is a diagram showing cross-correlation of the overall response of each part highlighted in the time-scale of FIG. 7 with the m-sequence associated with the q-th cell to obtain the current response of the q-th cell when the m-sequence has just ended.

At the conclusion of each m-sequence, after each time period of length N*Ts has elapsed, it is possible to calculate the response of every cell based upon on the data gathered during the execution time of the m-sequence just completed. According to one arrangement, the response of the q-th cell, with which the q-th m-sequence obtainable through a cyclic translation of q symbols of the mother m-sequence is associated, is of interest to the user. As shown in FIG. 8, the data corresponding to the overall response of each part highlighted in the time-scale shown in FIG. 7 may be cross-correlated with the m-sequence associated with the q-th cell, in order to obtain the current response of the q-th cell for the m-sequence that just concluded.

Once a period of time equal to a whole number n of m-sequences has elapsed, it is possible to calculate the average response of each cell using the responses of each cell derived from data collected during the first, second, and up to the n-th stimulation m-sequence.

According to a further aspect of this disclosure, and alternatively, the calculation of the response of every cell is updated at the end of every symbol time equal to T/N. In this manner, the user may now follow the evolution of the calculated response for each cell in real time without waiting until the end of an m-sequence. This has been found considerably advantageous not only in time savings, but also in providing immediate displaying to the user of the effectiveness of the result and possible errors.

Figure 9:
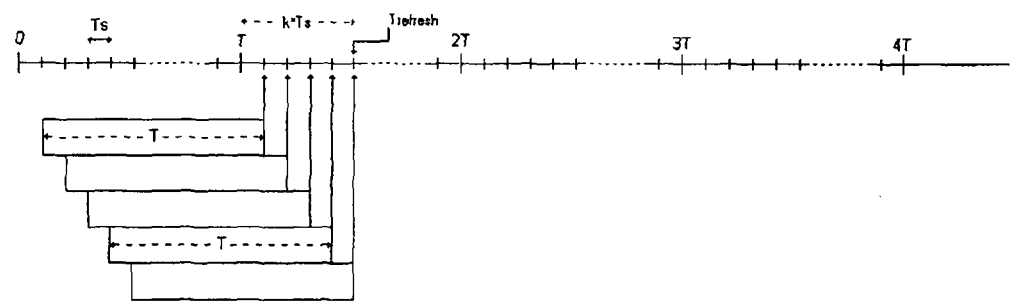
FIG. 9 illustrates a time-scale, according to a further aspect of the disclosure, where k is equal to a whole number of time periods, Ts, that follow the end of the previous m-sequence after which an update is desired as to the wave-forms for the responses of the various cells, and wherein a part of overall response of length N*Ts that goes from the moment $T_{refresh}$ at which an update is desired, up to $T_{refresh}$–N*Ts.
Figure 10:
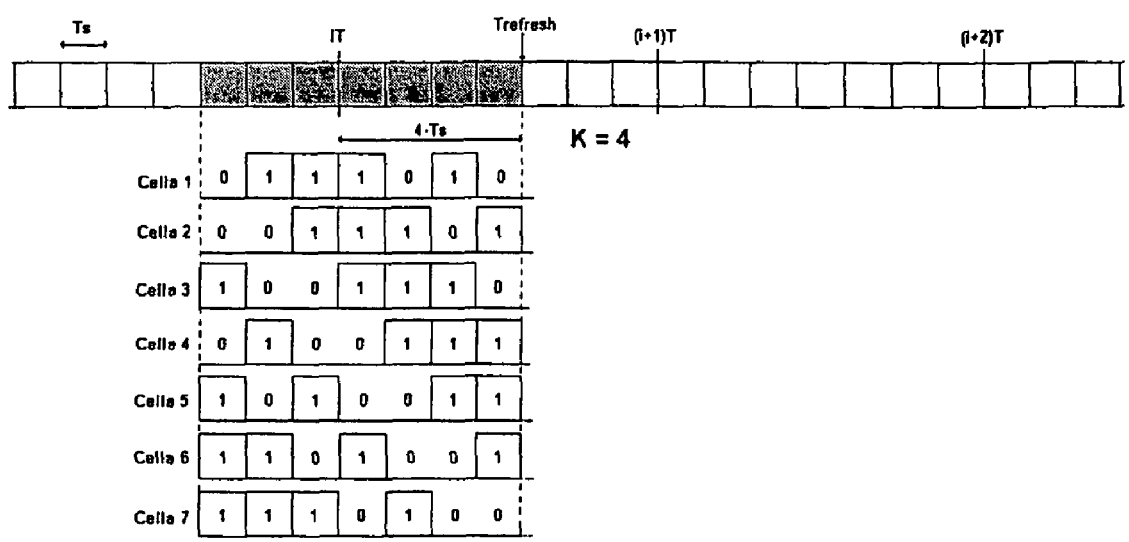
FIG. 10 is a diagram representing, for each cell, the sequences to be cross-correlated with the overall response acquired in the time period from $T_{refresh}$ up to $T_{refresh}$–N*Ts, where k=4 and the set of m-sequences used is the one previously represented.

The foregoing is demonstrated by the following example, shown in FIG. 9. Initially, it is assumed that k equals a whole number of time periods Ts that follow the end of the previous m-sequence, after which an update is desired for the waveforms of the responses of the various cells. Such is considered to be the part of the overall response time of length N*Ts that goes from the moment $T_{refresh}$ at which an update is wanted, up to $T_{refresh}-N*Ts$.

According to another aspect of this disclosure., the response of the q-th cell, with which at the beginning the q-th m-sequence obtainable through a cyclic translation of q symbols of the mother m-sequence is associated, is of interest. In this scenario, the data extracted from the overall response (namely, from $T_{refresh}$ up to $T_{refresh}-N*Ts=T_{refresh}-T$) must be cross-correlated not with the m-sequence associated with the q-th cell but rather with a version thereof that is delayed cyclically by k symbols to obtain the current response of the q-th cell due to the N most recent stimuli (generated in a selected time period T). This is demonstrated by the diagram set forth in FIG. 10 in which, for each cell, the sequences to be cross-correlated with the overall response acquired in the time period from $T_{refresh}$ up to $T_{refresh}-N*Ts$ are represented. In this example, k=4 and the set of m-sequences used is the one represented previously.

This partial result may be used to calculate the average response associated with the q-th cell in combination with the partial results calculated previously for the same cell. The calculated wave-forms associated with the various cells can either be directly interpreted or associated with a pattern made up of luminous, isoluminant or gray-scale chromatic stimuli that mirror the stimuli matrix.

In summary, displaying the results in real-time allows the medical system operator or, in the alternative, permits the processor to automatically:

monitor potential loss of attention by the patient or possible artifacts that can contaminate and, in turn, jeopardize the outcome of the patient's examination;

interrupt the acquisition cycle of the biopotential at any time; and repeat only the stimulus portion of the examination where an artifact of the biopotential, which is associated with the responses generated by specific cells, has been identified.

As a result, not only is the duration of examination reduced significantly, but also the attention, learning and fatigue capability of the patient is optimized. This also advantageously provides an instantaneous evaluation element for an intrinsic coefficient of variation (CV) and a standard error of the mean (SEM) in real-time, and, at the same time, the qualitative analysis of the result.

According to the analysis strategy selected, it is apparent that during the acquisition process the bioelectric responses so calculated $$\overline{A} = \sum_{0}^{N_C-1} {}_i A_i$$

$$\sigma_A = \sqrt{\frac{1}{N_c - 1} \sum_{0}^{N_c-1} \cdot (A_i - \overline{A})^2}$$

could could differ from the corresponding responses determined previously. The coefficient of variation (CV) provides instantaneously the standard deviation of the measurements, i.e., the root mean square $\sigma_A$ of the responses calculated in successive time periods purged of the mean value $\overline{A}$.

The standard error of the mean (SEM), which equals the standard deviation of the samples measured divided by the root of the number Nc of samples measured, is used to evaluate the reliability of the measurement. It is noted that although such a parameter cannot be tested clinically, it provides the system operator or user with data on how accurate statistically the phenomenon has been characterized.

$$CV = \frac{\sigma_A}{\overline{A}}$$

$$SEM = \frac{\sigma_A}{\sqrt{N_c}}$$

It is noted that although such a parameter cannot be tested clinically, it provides the system operator with data on how accurate statistically the phenomenon has been characterized.

Advantageously, by the present invention, it is now possible to compare the results obtained from the patient examined with a standard normalized database derived from extensive statistics collected on samples of normal subjects, indicating deviation of the subject from an average of the normal subjects relative to age. For example, a statistical test of 154 healthy eyes was conducted in order to define the normal ranges for size and latency of the bioelectric responses correlated with the retinal surface stimulated by various electrofunctional examinations. The statistical analysis was performed on a population of normal subjects to establish and correlate normal ranges with the age of the patient. The examinations considered belong to a variegated population of patients from a minimum age of 12 up to a maximum age of 87. The results obtained show a dependence of size and latency on the age of the patient. Such normative or analogous data, after having been evaluated statistically, can then be input into the apparatus as a physiological parameter of "normality" so as to enable the user to quickly and effectively consult the same.

In this manner, unlike conventional techniques, the present invention allows the user to achieve a result that is untainted by variable intrinsic factors, such as loss of focus or eye movements. The apparatus, as described in the example above, allows examination of a single eye or of both eyes of the patient simultaneously. According to a further arrangement, illustrated schematically in FIG. 3, it is necessary to examine only one eye at a time. Moreover, such a solution ensures even greater precision of the results, thereby avoiding contamination of the biopotential with possible unreliable recordings.

Figure 3:
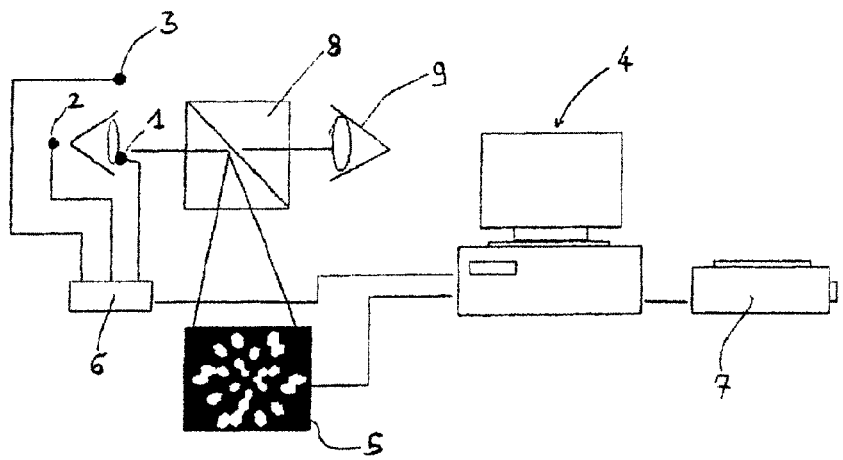
FIG. 3 shows schematically a hardware system, according to another aspect of the disclosure.

In particular, the apparatus illustrated in FIG. 3 differs from the apparatus described in the previous example in that a mirror or prism 8 for optical beam separation (also known as a beam splitter, e.g., of a conventional type) is positioned between the eye of the patient and the pattern stimulator (CRT, CCD, LED, OLED, PLASMA). The beam splitter, also arranged in a suitable position on the optical path, allows the patient to be shown a visual stimulus, while at the same time the operator is shown an image of the relevant portion of the patient's eye.

Using an ophthalmoscope (not shown), the medical operator, corresponding to eye 9 in the drawings, either directly or using a camera linked to a monitor, can therefore observe the base of the patient's retina during examination, thereby ensuring that the stimulus is projected exactly at the centre of the fovea.

Hence, the user is able to instantly make corrections, interrupting and then continuing the stimulus associated with the response of the stimulated area (due to real-time control according to this disclosure), whether resulting from the loss of focus of the patient on the stimulus, or due, for instance, to eye movement, blinking or attention difficulties following the examination itself. In addition, the operator may temporarily interrupt the recording, in the event that the patient experiences slight momentary difficulties as the examination progresses. Providing exact projection of the stimulus in the foveal area minimizes unreliable measurements caused when a patient has difficulties during examination.

Figure 5:
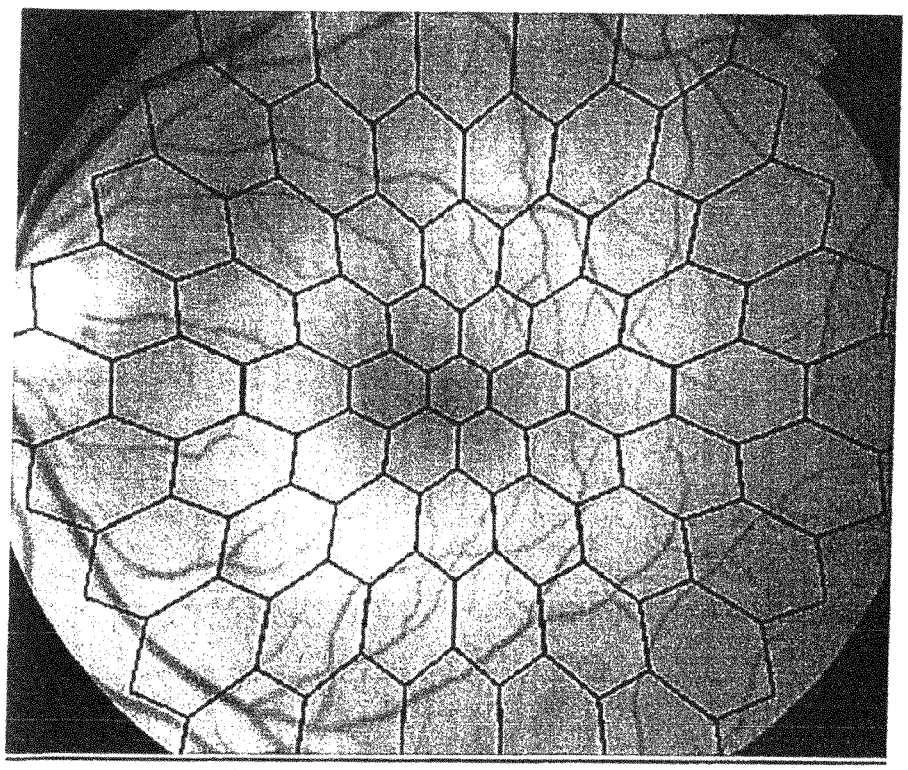
FIG. 5 is an image representing a display that can be obtained by a medical operator using the system set forth in FIG. 3; B10
Figures 6, 7:
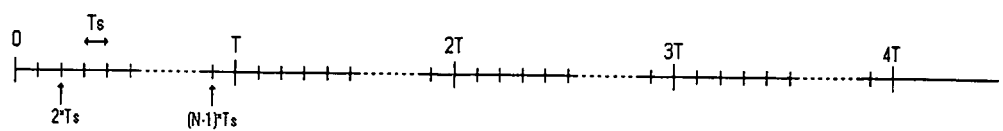
FIG. 6 illustrates pseudo-orthogonal m-sequences generated by cyclic translation of a mother m-sequence, in accordance with one aspect of the disclosure.
FIG. 7 shows a time-scale of a series of m-sequences, according to another aspect of the disclosure.

In a particularly advantageous arrangement of the present invention, the beam splitter, the ophthalmoscope, the real-time photography of the fundus oculi and the focusing of the stimulus on the desired retinal areas, the system for collimation, pointing and correcting the refractive error or ametropia of the patient, and a suitable optical system for projecting the pattern are stably integrated in a single optical-mechanical-electronic assembly, such that the view field of the ophthalmoscope and the projection field of the pattern match up exactly and definitively. FIG. 5 illustrates the matching-up of the response generated by each individual cell with the image of the patient's fundus oculi.

Accordingly, and also pursuant to a conventional comparison between the response obtained from the patient with the normality data correlated with the age of the subject obtained from clinical testing, system operation is now accomplished much more precisely and reliably. This, in turn, reduces substantially the coefficient of variability of the current technique. As a result, diagnosis is obtained independent of and unaffected by both the system operator's ability and any interference from the patient, as well as those of the other factors and sources of variability described above.

Moreover, in both arrangements, the ability to archive the results obtained for subsequent diagnosis makes it possible to monitor the progress of the patient's pathology over time, and the passible effectiveness of pharmacological treatment.

What is claimed is:

1. A process for determining the topography of bioelectric response signals of a visual system of a patient, the patient's retina, optical nerve or a projection thereof being at the level of the central cortex, following visual stimulation through a surface arranged in front of the patient's eye, wherein an image which comprises a plurality of cells is displayed as stimulation, each cell being activated or deactivated according to a corresponding digital time function represented by a cyclical succession of binary m-sequences of duration (T) formed by a plurality of activation symbols (N), each having a duration (Ts), the m-sequences of the various cells being obtained cyclically from a mother m-sequence, the process determining the total bioelectric response of the visual system, the response associated with each cell being determined by the total response of the visual system using a cross-correlation with a suitable translated version of a mother m-sequence, wherein calculation of the response of each cell is updated at the end of each symbol time (Ts), thereby making it possible to follow the evolution of the calculated response of each cell in real-time, without awaiting the end of an m-sequence.

2. The process set forth in claim 1, wherein updating is accomplished, after a certain number (k) of symbol times (Ts) to obtain the response of a q-th cell associated with an m-sequence translated by a number (q) of symbols from the mother m-sequence, by cross-correlating the data extracted from the overall response not with the translated m-sequence, but with a version thereof cyclically delayed by the number (k) to obtain the current response of the q-th cell due to a number (N) of most recent stimuli.

3. The process set forth in claim 1, wherein the calculated wave-forms associated with the various cells are either directly interpreted or are associated with a pattern comprising luminous, isoluminant or gray-scale chromatic stimuli that mirrors the matrix of the stimuli.

4. The process set forth in claim 1, wherein the accuracy of the acquisition step is evaluated based on an intrinsic coefficient of variation (CV) and upon a standard error of the mean (SEM) of the result obtained in real-time.

5. The process set forth in claim 4, wherein the intrinsic coefficient of variation (CV) and the standard error of the mean (SEM) are calculated in accordance with $$CV = \frac{\sigma_A}{\bar{A}} \text{ and } SEM = \frac{\sigma_A}{\sqrt{N_c}}.$$

6. The process set forth in claim 1, wherein the result obtained by the patient examined is compared with a normative database that includes results obtained on normal subjects, to indicate the deviation of the subject compared to the average of the normal subjects in relation to age.

7. A system for determining the topography of bioelectric response signals of a visual system of a patient including the patient's retina, optical nerve or a projection thereof at the level of the central cortex, following visual stimulation, the system comprising a display arranged in front of the patient's eye, a processor connected to the display for showing an image, as stimulation, including a plurality of cells, each cell being activated or deactivated according to a corresponding digital time function represented by a cyclical succession of binary m-sequences of duration (T) formed by a plurality of activation symbols (N), each having a duration (Ts), the m-sequences of the various cells being obtained cyclically from a mother m-sequence, the system further comprising a sensor and amplifier for determining the total bioelectric response of the visual system, and recording the response on the processor, such that the response associated with each cell is determined by the total response of the visual system using a cross-correlation with a suitable translated version of a mother m-sequence, wherein the processor updates the calculation of the response of each cell at the end of every symbol time (Ts), thereby making it possible to follow the evolution of the calculated response of each cell in real-time without having to wait for the end of an m-sequence.

8. The system forth in claim 7, wherein the processor performs the updating operation, after a selected number (k) of symbol times (Ts) to obtain the response of a q-th cell associated with an m-sequence translated by a number (q) of symbols from the mother m-sequence, by cross-correlating the data extracted from the overall response not with the translated m-sequence, but with a version thereof cyclically delayed by the number (k) to obtain the current response of the q-th cell due to a number (N) of most recent stimuli.

9. The system set forth in claim 7, wherein the processor interprets either the calculated wave-forms associated with the various cells directly or those associated with a pattern made up of luminous, isoluminant or gray-scale chromatic stimuli that mirrors the matrix of the stimuli.

10. The system set forth in claim 7, wherein the processor evaluates the accuracy of the acquisition step based on an intrinsic coefficient of variation (CV) and a standard error of the mean (SEM) of the result obtained in real-time.

11. The system set forth in claim 10, wherein the intrinsic coefficient of variation (CV) and the standard error of the mean (SEM) are calculated in accordance with $$CV = \frac{\sigma_A}{\bar{A}} \text{ and } SEM = \frac{\sigma_A}{\sqrt{N_c}}.$$

12. The system set forth in claim 7, wherein the processor comprises a storage member of a normative database that includes results obtained on normal subjects, the result obtained from the patient examined being compared to the database, so as to indicate deviation of the subject compared to the average of normal subjects relative to age.

13. The system set forth in claim 7, wherein between the patient and the display, an optical beam separator is arranged, suitable for allowing the patient to observe the stimulation reflected by the divider instead of directly from the display, thus enabling a medical operator, for control purposes, to observe the retina base of the patient during the course of examination.

14. The system set forth in claim 13, wherein the optical beam separator, the display and ophthalmoscopic member for observing the retina base of the patient during the course of examination, are stably integrated in a single optical-mechanical assembly.

15. A program-controlled apparatus for determining the topography of bioelectric response signals of a visual system of a patient, the patient's retina, optical nerve or a projection thereof being at the level of the central cortex, following visual stimulation through a surface arranged in front of the patient's eye, which performs the steps of: (i) displaying an image comprising a plurality of cells as stimulation, each cell being activated or deactivated according to a corresponding digital time function represented by a cyclical succession of binary m-sequences of a first selected duration formed from a plurality of activation symbols, each having a second selected duration, the m-sequences of the various cells being obtained cyclically from a mother m-sequence; (ii) determining the total bioelectric response of the visual system, the response associated with each cell being determined by the total response of the visual system by a cross-correlation with a suitable translated version of a mother m-sequence, wherein calculation of the response of each cell is updated at the end of each symbol time (Ts), thereby making it possible to follow the evolution of the calculated response of each cell in real-time, without awaiting the end of an m-sequence.

16. The apparatus set forth in claim 15, wherein the process is stored in a memory support device.

17. The apparatus set forth in claim 15, wherein the process is stored in the processor of the system.

* * * * *